United States Patent
Franklin et al.

(10) Patent No.: US 10,632,052 B2
(45) Date of Patent: *Apr. 28, 2020

(54) ANTIPERSPIRANT COMPOSITIONS

(71) Applicant: Conopco, Inc., Englewood Cliffs, NJ (US)

(72) Inventors: Kevin Ronald Franklin, Wirral (GB); Neil Robert Fletcher, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/772,708

(22) PCT Filed: Oct. 4, 2016

(86) PCT No.: PCT/EP2016/073661
§ 371 (c)(1),
(2) Date: May 1, 2018

(87) PCT Pub. No.: WO2017/076562
PCT Pub. Date: May 11, 2017

(65) Prior Publication Data
US 2018/0318187 A1   Nov. 8, 2018

(30) Foreign Application Priority Data
Nov. 6, 2015  (EP) .................................... 15193410

(51) Int. Cl.
| | | |
|---|---|---|
| *A61K 8/26* | (2006.01) | |
| *A61K 8/44* | (2006.01) | |
| *A61Q 15/00* | (2006.01) | |
| *A61K 8/20* | (2006.01) | |
| *A61K 8/19* | (2006.01) | |

(52) U.S. Cl.
CPC ................. *A61K 8/26* (2013.01); *A61K 8/19* (2013.01); *A61K 8/20* (2013.01); *A61K 8/44* (2013.01); *A61Q 15/00* (2013.01); *A61K 2800/805* (2013.01); *A61K 2800/874* (2013.01)

(58) Field of Classification Search
CPC ... A61K 8/26; A61K 8/44; A61K 8/20; A61K 8/19; A61K 2800/874; A61K 2800/805; A61Q 15/00
See application file for complete search history.

(56) References Cited

U.S. PATENT DOCUMENTS

| | | |
|---|---|---|
| 2,210,013 A | 8/1940 | Teller |
| 2,412,535 A | 12/1946 | Richardson et al. |
| 3,666,668 A | 5/1972 | Klausner |
| 3,766,233 A | 10/1973 | Tsukada |
| 3,792,068 A | 12/1974 | Luedders et al. |
| 4,183,911 A | 1/1980 | Smithies et al. |
| 4,359,456 A | 11/1982 | Gosling et al. |
| 4,369,173 A | 1/1983 | Causland et al. |
| 4,435,382 A | 3/1984 | Shin et al. |
| 5,348,731 A | 9/1994 | Patti et al. |
| 5,681,802 A | 10/1997 | Fujiwara et al. |
| 5,744,130 A | 4/1998 | Guskey et al. |
| 5,814,309 A | 9/1998 | Panitch |
| 5,911,977 A | 6/1999 | Brewster et al. |
| 5,955,065 A | 9/1999 | Thong et al. |
| 6,024,945 A | 2/2000 | Parekh |
| 6,042,816 A | 3/2000 | Shen |
| 6,096,297 A | 8/2000 | Jones et al. |
| 6,136,303 A | 10/2000 | Ruebusch et al. |
| 6,261,543 B1 | 7/2001 | Fletcher et al. |
| 6,383,476 B1 | 5/2002 | Scavone et al. |
| 6,511,243 B2 | 1/2003 | Miranda |
| 6,911,195 B2 | 6/2005 | Vu et al. |
| 6,942,850 B2 | 9/2005 | Coe et al. |
| 7,087,220 B2 | 8/2006 | Li |
| 7,704,531 B2 | 4/2010 | Tang et al. |
| 9,775,791 B2 | 10/2017 | Fawzy et al. |
| 9,867,765 B2* | 1/2018 | Franklin .................. A61K 8/26 |
| 10,117,814 B2 | 11/2018 | Duncan |
| 2002/0012565 A1 | 1/2002 | Sirna et al. |

(Continued)

FOREIGN PATENT DOCUMENTS

| | | |
|---|---|---|
| CN | 1323191 | 11/2001 |
| DE | 19962878 | 6/2001 |

(Continued)

OTHER PUBLICATIONS

IRPR2 in PCTEP2015074529; Dec. 2, 2016.
Search Report & Written Opinion in PCTEP2016080034; dated Feb. 9, 2017.
Search Report in PCTEP2014059582; dated Oct. 6, 2014.
Written Opinion 1 in PCTEP2014059583; dated Oct. 6, 2014.
Written Opinion in PCTEP2014059582; dated Oct. 6, 2014.
Search Report in PCTEP2014059583; dated Oct. 6, 2014.
Search Report in PCTEP2014060306; dated Oct. 6, 2014.
Written Opinion in PCTEP2014060306; dated Oct. 6, 2014.
Karl Laden; Chemistry of Aluminum-Zirconium-Glycine (AZG) Complexes; Antiperspirants and Deodorants; 1999; pp: cover pages, title pages & p. 137 (total of 4 pages); vol. 20, Second Edition.

(Continued)

*Primary Examiner* — Blessing M Fubara
(74) *Attorney, Agent, or Firm* — Greenberg Traurig, LLP

(57) ABSTRACT

An aqueous composition comprising basic aluminium chloride salt of formula $Al_2(OH)_{4.4}Cl_{1.6}$ to $Al_2(OH)_{4.9}Cl_{1.1}$, calcium chloride at a molar level of 0.020 or greater relative to the aluminium present, and glycine at a molar level of 0.050 or greater relative to the aluminium present, characterised in that the molar ratio of aluminium to the sum of the molar amounts of the calcium chloride and glycine is from 3.9:1 to 6.1:1 and in that the molar ratio of glycine to Al is greater than 1.7:10 and the molar ratio of Ca to Al is less than 0.35:10 or the molar ratio of Ca to Al is greater than 0.35:10 and the molar ratio of glycine to Al is less than 1.7:10.

18 Claims, No Drawings

(56) References Cited

U.S. PATENT DOCUMENTS

| | | |
|---|---|---|
| 2002/0125462 A1 | 9/2002 | McKie et al. |
| 2003/0049219 A1 | 3/2003 | Lemoine et al. |
| 2003/0215399 A1 | 11/2003 | Smith et al. |
| 2003/0215408 A1 | 11/2003 | Dees |
| 2004/0115147 A1 | 6/2004 | Vu et al. |
| 2005/0163737 A1 | 7/2005 | Lemoine et al. |
| 2006/0153788 A1 | 7/2006 | Swaile et al. |
| 2006/0204463 A1 | 9/2006 | Tang et al. |
| 2006/0222612 A1 | 10/2006 | Ni et al. |
| 2007/0020211 A1 | 1/2007 | Li et al. |
| 2007/0148113 A1 | 6/2007 | Lemoine et al. |
| 2007/0148443 A1 | 6/2007 | Blum et al. |
| 2007/0172440 A1 | 7/2007 | Schulz et al. |
| 2007/0196303 A1 | 8/2007 | Li et al. |
| 2007/0286830 A1 | 12/2007 | Li et al. |
| 2007/0292358 A1 | 12/2007 | Emmerling et al. |
| 2008/0131354 A1 | 6/2008 | Li et al. |
| 2008/0241089 A1 | 10/2008 | Banowski et al. |
| 2008/0267895 A1 | 10/2008 | Franklin et al. |
| 2009/0018044 A1 | 1/2009 | Dreja et al. |
| 2009/0104281 A1 | 4/2009 | Taylor et al. |
| 2009/0232746 A1 | 9/2009 | Mateu et al. |
| 2009/0311195 A1 | 12/2009 | Clarke et al. |
| 2009/0317347 A1 | 12/2009 | Popoff et al. |
| 2010/0303749 A1 | 12/2010 | Pan |
| 2011/0038822 A1 | 2/2011 | Phipps et al. |
| 2011/0038823 A1 | 2/2011 | Phipps et al. |
| 2011/0038902 A1 | 2/2011 | Phipps et al. |
| 2011/0217254 A1 | 9/2011 | Miertsch et al. |
| 2011/0274637 A1 | 11/2011 | Milardovic et al. |
| 2013/0164238 A1 | 6/2013 | Banowski et al. |
| 2013/0273274 A1 | 10/2013 | Mueller et al. |
| 2014/0079649 A1 | 3/2014 | Swaile |
| 2014/0173833 A1 | 6/2014 | Banowski et al. |
| 2014/0178321 A1 | 6/2014 | Banowski et al. |
| 2014/0301963 A1 | 10/2014 | Claas et al. |
| 2015/0118173 A1 | 4/2015 | Farwick et al. |
| 2016/0106649 A1 | 4/2016 | Fawzy et al. |
| 2016/0113850 A1 | 4/2016 | Fawzy et al. |
| 2018/0140522 A1 | 5/2018 | Doering et al. |

FOREIGN PATENT DOCUMENTS

| | | |
|---|---|---|
| EP | 0308937 | 3/1989 |
| EP | 0343843 | 11/1989 |
| EP | 0405598 | 1/1991 |
| EP | 0674899 | 10/1995 |
| EP | 1104282 | 6/2001 |
| EP | 1550435 | 7/2005 |
| EP | 2481392 | 8/2012 |
| EP | 2999452 | 12/2017 |
| GB | 811079 | 4/1959 |
| GB | 813767 | 5/1959 |
| GB | 1024501 | 3/1966 |
| GB | 1268200 | 3/1972 |
| GB | 1285073 | 8/1972 |
| GB | 1347950 | 2/1974 |
| GB | 1362495 | 8/1974 |
| GB | 1555044 | 11/1979 |
| GB | 1589229 | 5/1981 |
| GB | 2113116 | 8/1983 |
| GB | 2299507 | 10/1996 |
| JP | 2014047186 | 3/2014 |
| WO | WO9604884 | 2/1996 |
| WO | WO9624326 | 8/1996 |
| WO | WO0001422 | 1/2000 |
| WO | WO0010512 | 3/2000 |
| WO | 1175165 | 4/2000 |
| WO | WO0127351 | 4/2001 |
| WO | WO2005007377 | 1/2005 |
| WO | WO2005018553 | 3/2005 |
| WO | 1576946 | 9/2005 |
| WO | WO2005105026 | 11/2005 |
| WO | WO2006050776 | 5/2006 |
| WO | WO2006062846 | 6/2006 |
| WO | WO2006091417 | 8/2006 |
| WO | WO2007124889 | 11/2007 |
| WO | WO2008063188 | 5/2008 |
| WO | WO2009044381 | 4/2009 |
| WO | WO2009075678 | 6/2009 |
| WO | WO2009076591 | 6/2009 |
| WO | WO2009076592 | 6/2009 |
| WO | WO2011016807 | 2/2011 |
| WO | WO2012010684 | 1/2012 |
| WO | WO2012021356 | 2/2012 |
| WO | WO2012060817 | 5/2012 |
| WO | WO2012061280 | 5/2012 |
| WO | WO2012098189 | 7/2012 |
| WO | WO2012148480 | 11/2012 |
| WO | WO2012148481 | 11/2012 |
| WO | WO2013064367 | 5/2013 |
| WO | WO2013158077 | 10/2013 |
| WO | WO2014095688 | 6/2014 |
| WO | WO2014147739 | 9/2014 |
| WO | WO 2014/187685 A1 * | 11/2014 |
| WO | WO2014187684 | 11/2014 |
| WO | WO2014187685 | 11/2014 |
| WO | WO2014187802 | 11/2014 |
| WO | WO2015091742 | 6/2015 |
| WO | WO2016066528 | 5/2016 |
| WO | WO2016078991 | 5/2016 |
| WO | WO2016198202 | 12/2016 |
| WO | WO2017076836 | 5/2017 |

OTHER PUBLICATIONS

Written Opinion in PCTEP2015074529; dated Sep 6, 2016.
Deodorant Roll-On; Deodorant Roll-On Product Data Sheets (D19A-J) ; Apr. 1, 2011; pp. 1-31.
Clinical Protection Antiperspirant Deodorant Cream; Deodorant Cream Product Data Sheets (D20A-D); Sep. 24, 2018; pp. 1-11.
Notice of Opposition in EP14725433 (EP2999452) (P&G); Sep. 24, 2018.
IRPR2 in PCTEP2015074528; Jan. 18, 2017.
IPRP in PCTEP2016080034 ; Feb. 14, 2018.
Search Report in EP14193902; dated May 6, 2015.
Written Opinion in EP14193902, dated May 6, 2015.
Written Opinion 2 in PCTEP2014059583; dated Apr. 30, 2015.
Search Report and Written Opinion in EP17199987; dated Dec. 6, 2017.
Search Report in EP14190531; dated May 8, 2015.
Written Opinion in EP14190531; dated May 8, 2015.
Search Report in EP14190530; dated Feb. 12, 2015.
Written Opinion in EP14190530; dated Feb. 12, 2015.
Pluronic(R) F-127; Newdruginfo.com; Jun. 7, 2016; 1 page.
Search Report & Written Opinion in PCTEP2015074528; dated Jan. 20, 2016.
Search Report & Written Opinion in PCTEP2015076365; dated Feb. 11, 2016.
Written Opinion in EP13168418; dated Oct. 31, 2013.
Search Report & Written Opinion in PCTEP2015074529; dated Dec. 21, 2015.
Search Report in EP13168418; dated Oct. 31, 2013.
Search Report in EP13168417; dated Oct. 31, 2013.
IPRP2 in PCTEP2014060306; Sep. 16, 2015.
Laden; Antiperspirants and Deodorants 1999 2nd Edition pp. 96-97;
Antiperspirants and Deodorants 1999 2nd Edition pp. 96-97; 1999; pp. 96-97; 2nd Edition.
Written Opinion in EP13168417; dated Oct. 31, 2013.
IPRP2 in PCTEP2014059583; Sep. 11, 2015.
Written Opinion 2 in PCTEP2014060306; dated May 8, 2015.
Search Report and Written opinion in PCTEP2019055000; dated Apr. 3, 2019.
Protective Deodorant Spray, Mintel GNPD, 2014, pp. 1-2; XP002756659.
IPRP2 in PCTEP2016073661, Oct. 27, 2017.
Search Report & Written Opinion in EP15193410, dated May 19, 2016.
Search Report and Written Opinion in PCTEP2016073661, dated Dec. 5, 2016.

(56) References Cited

OTHER PUBLICATIONS

Co-Pending Application, Sebastian Alvarez, Filed May 1, 2018
Search Report and Written Opinion in EP18164854; dated Jul. 30, 2018.
Search Report and Written Opinion in EP17200556; dated Apr. 11, 2018.
Amodimethicone; Saapedia; May 21, 2015; pp. 1-3; "www.saapedia.org/en/saa/?type-detail&id-1885".; .; United States of America.
Search Report & Written Opinion in PCTEP2015075419; dated Jan. 21, 2016.
Anonymous; Aluminum Zirconium Chlorohydrex Complexes with Glycine; Cosmeticsinfo.org; 2015; pp. 1-3 Retrieved from the Internet: http://www.cosmeticsinfo.org/ingredient/aluminum-zirconium-chlorohydrex-complexes-glycine [retrieved on Dec. 7, 2015] XP055234010.
Apr. 2014 Teacher's Guide for (Under) Arm Yourself with Chemistry!; acs.orgichemmatters; Apr. 2014; pp. 1-38 Retrieved from Internet: http://www.acs.org/content/dam/acsorg/education/resources/highschool/chemmatters/teacherguide/chemmatters-tg-april12014-deodorant.doc retrieved Dec. 7, 2015 XP055234066.
Ant-Perspirant Deodorant Roll-On; Mintel GNPD Database; Nov. 1, 2014; pp. 1-2; XP002739560; Germany.
Anti-Perspirant Deodorant Roll-on; Mintel GNPD Database; Apr. 1, 2012; pp. 1-2; XP002739559; United Kingdom.
Search Report in EP15150655; dated Jun. 22, 2015; European Patent Office (EPO).
Written Opinion in EP15150655; dated Jun. 22, 2015; European Patent Office (EPO).
Search Report and Written Opinion in PCTEP2018079947; dated Jan. 2, 2019.
Portective Deodorant Spray; Database GNPD Mintel; 2014; pp. 1-2; XP002756659; Mexico.
Search Report and Written Opinion in PCTEP2016076311; dated Dec. 23, 2016.
Written Opinion 2 in PCTEP2016076306; dated Sep. 14, 2017.
Search Report & Written Opinion in EP15193404; dated May 9, 2016; European Patent Office (EPO).
Search Report & Written Opinion in EP15193409; dated Apr. 18, 2016.
Search Report and Written Opinion in PCTEP2016076306; dated Jan. 23, 2017.
Mintel GNPD; Sensitive Skin Deodorant Spray, Lactovit; Mintel GNPD; Jul. 2013; pp. 1-3, Record ID 2102829.
Mintel GNPD; Protective Deodorant, Lactovit Activit; Mintel GNPD; Sep. 2013; pp. 1-3 Record ID 2192256.
Mintel GNPD; Repairing Deodorant, Lactoit Lacourea 10; Mintel GNPD; Aug. 2014; pp. 1-2 Record ID 2619709.
Mintel GNPD; Deodorant Extra-Efficiency, Lactovit Original; Mintel GNPD; Jul. 2013; pp. 1-2 Record ID2121626
Edited by Barel, et al.; Handbook of Cosmetic Sience and Technology; Handbook of Cosmetic Sience and Technology; Apr. 9, 2014; pp. 1-2 (Cover & summary); 4th Edition.
Edited by Barel, et al.; Section 48—Antiperspriants and Section 49—Deodorants; Handbook of Cosmetic Science and Technology; Apr. 9, 2014; pp. 1-19 (cover pp. and pp. 505-518; 4th Ed.
Regulations; Official Journal of the European Union; dated Mar. 9, 2012; pp. 1-295 or L83/1-L83/295.

\* cited by examiner

ANTIPERSPIRANT COMPOSITIONS

The present invention is concerned with antiperspirant compositions and with methods of making the same. It is particularly concerned with the compositions comprising basic aluminium chloride (herein BAC) antiperspirant actives and their manufacture.

The compositions of the present invention may be used as antiperspirant compositions and/or may be used in the manufacture of high efficacy antiperspirant compositions. Using the processes described herein, particularly effective or "activated" BAC compositions may be prepared.

Certain activated BAC actives are commercially available and their preparation and use are disclosed in numerous publications.

Traditionally, activated BAC samples have been prepared by prolonged heating of BAC solutions followed by spray drying; see, for example, U.S. Pat. No. 4,359,456 (Gosling). The samples prepared by this method needed to be formulated into essentially anhydrous compositions in order for the antiperspirant to maintain its high activity.

Activated BAC samples have also been prepared using water soluble calcium acids, particularly with a further adjunct such as an amino acid, hydroxyl acid, or betaine. Some of these samples could be formulated into aqueous compositions without the antiperspirant losing all of its enhanced activity.

EP 1,104,282 (Gillette) discloses a means of producing activated BAC samples using a water soluble calcium salt and an amino acid or a hydroxy acid.

U.S. Pat. No. 6,911,195 (Gillette) discloses water-in-oil emulsion gels comprising aluminium-zirconium antiperspirant salts activated using calcium ions.

U.S. Pat. No. 5,955,065 (Gillette) discloses anhydrous suspension formulations comprising particulate BAC and aluminium-zirconium antiperspirant salts activated using calcium ions.

U.S. Pat. No. 6,942,850 (Gillette) discloses aqueous alcoholic composition comprising aluminium-zirconium antiperspirant salts activated using calcium ions.

WO 2009/044381 (P&G) discloses water-in-oil emulsion sticks comprising BAC and aluminium-zirconium antiperspirant salts activated using calcium ions.

U.S. Pat. No. 7,704,531 (Colgate) discloses compositions comprising an active system made from combining an aluminium or aluminium-zirconium salt, a calcium salt, and a betaine.

US 2011/0038823 (Dial/Henkel) discloses water-in-oil emulsion sticks comprising an antiperspirant active prepared by combining BAC, calcium chloride and glycine.

US 2007/196303, US 2007/0020211, WO 2008/063188, US 2008/0131354 and U.S. Pat. No. 7,087,220 (Summit and Reheis) each describe methods of making calcium-activated antiperspirant salts.

WO 2009/075678, WO 2009/076592, WO 2011/016807, WO 2012/060817, WO 2012/061280, WO 2012/148480 and WO 2012/148481 (Colgate) disclose the manufacture of activated antiperspirant salts by neutralisation of aluminium chloride with calcium hydroxide in the presence of glycine.

The present invention is particularly concerned with BAC compositions comprising aluminium sesquichlorohydrate (herein ASCH) of chemical formula $Al_2(OH)_{4.4}Cl_{1.6}$ to $Al_2(OH)_{4.9}Cl_{1.1}$. This material is commercially available, but its formulation and use described herein are new and deliver unexpected benefits.

In a first aspect of the present invention, there is provided an aqueous composition comprising:

(i) basic aluminium chloride (BAC) salt of formula $Al_2(OH)_{4.4}Cl_{1.6}$ to $Al_2(OH)_{4.9}Cl_{1.1}$,
(ii) calcium chloride at a molar level of 0.020 or greater relative to the aluminium present in the BAC salt, and
(iii) glycine at a molar level of 0.050 or greater relative to the aluminium present in the BAC salt, characterised in that the molar ratio of aluminium to the sum of the molar amounts of the calcium chloride and glycine is from 3.9:1 to 6.1:1 and in that:

(a) the molar ratio of glycine to Al is at least 1.7:10 and the molar ratio of Ca to Al is no more than 0.35:10 or the molar ratio of Ca to Al is at least 0.35:10 and the molar ratio of glycine to Al is no more than 1.7:10.

In a second aspect of the present invention, there is provided a method of manufacture of an aqueous antiperspirant composition, the method comprising:

(i) mixing basic aluminium chloride (BAC) salt of formula $Al_2(OH)_{4.4}Cl_{1.6}$ to $Al_2(OH)_{4.9}Cl_{1.1}$, calcium chloride at a molar level of 0.020 or greater relative to the aluminium present in the BAC salt, glycine at a molar level of 0.050 or greater relative to the aluminium present in the BAC salt, and water, such that the molar ratio of aluminium to the sum of the molar amounts of the calcium chloride and glycine is from 3.9:1 to 6.1:1; and (a) the molar ratio of glycine to Al is at least 1.7:10 and the molar ratio of Ca to Al is no more than 0.35:10 or
(b) the molar ratio of Ca to Al is at least 0.35:10 and the molar ratio of glycine to Al is no more than 1.7:10;

(ii) heating the mixture to a temperature of at least 65° C. for at least 2 hours, and
(iii) cooling the mixture to ambient temperature.

In a third aspect of the present invention, there is provided a method of attaining an antiperspirant benefit comprising the topical application to the surface of the human body of a composition according to the first aspect of the invention, especially when manufactured in accordance with the second aspect of the invention.

Aqueous compositions according to the first aspect of the invention may be used in the method of manufacture according to the second aspect of the invention. Aqueous compositions resulting from such a process have excellent antiperspirancy performance and storage stability.

Herein, the "activation mixture" refers to the mixture of basic aluminium chloride salt of formula $Al_2(OH)_{4.4}Cl_{1.6}$ to $Al_2(OH)_{4.9}Cl_{1.1}$, water soluble calcium chloride, glycine, and water.

The choice of BAC salt used is important to the success of the present invention. We have found that surprisingly good results are found on using BAC salts commonly referred to as aluminium sesquichlorohydrate (herein ASCH) having the chemical formula $Al_2(OH)_{4.4}Cl_{1.6}$ to $Al_2(OH)_{4.9}Cl_{1.1}$. Most commercial ASCH samples are of chemical formula $Al_2(OH)_{4.9}Cl_{1.1}$ and it is preferred to use BAC salts of this formula.

The surprisingly good results referred to in the above paragraph include surprisingly good antiperspirancy performance, particularly bearing in mind the relatively low Band III content of the aluminium actives typically employed. In addition, compositions prepared according to the present invention have remarkable rheological stability.

We have also observed that compositions according to the present invention may have improved colour stability, by which is meant that they exhibit reduced yellowing on storage, especially on storage at elevated temperature.

The BAC salt used in the present invention has aluminium to chloride molar ratio of from 1.25:1 to 1.82:1 and preferably 1.54:1 to 1.82:1.

Herein, references to (molar) amounts of aluminium, including references to "aluminium present" and ratios refer to the aluminium present in the BAC salt.

In order for the antiperspirant to become activated, it is important to have sufficient calcium and glycine present, relative to the amount of aluminium present. The molar ratio of calcium to aluminium is at least 1:50 and preferably at least 1:40 (i.e. 0.025:1) and the molar ratio of glycine to aluminium is at least 1:20 and preferably at least 1:10 (i.e. 0.1:1). Further, it is required that the molar ratio of the sum of the molar amounts of the calcium chloride and glycine to aluminium is at least 1:6.1 and preferably at least 1:6.0.

Surprisingly, it has also been observed that the storage stability of aqueous solutions of ASCH activated in accordance with the invention is critically dependent upon the levels of both calcium and glycine not being too high relative to the level of aluminium. For this reason, it is essential that the molar ratio of the sum of the molar amounts of the calcium chloride and glycine to aluminium is no greater than 1:3.9 and preferably no greater than 1:4.0.

In order to balance the activation achieved versus the storage stability, it is essential that the molar ratio of aluminium to the sum of the molar amounts of the calcium chloride and glycine is from 3.9:1 to 6.1:1; and preferred that it is from 4:1 to 6:1.

Balancing the activation achieved versus the storage stability also requires either a relatively high ratio of calcium to aluminium and a relatively low ratio of glycine to aluminium or, vice versa, a relatively high ratio of glycine to aluminium and a relatively low ratio of calcium to aluminium. Thus, it is required that either the molar ratio of glycine to Al is at least 1.7:10 and the molar ratio of Ca to Al is no more than 0.35:10 or the molar ratio of Ca to Al is at least 0.35:10 and the molar ratio of glycine to Al is no more than 1.7:10.

Preferred compositions have a molar ratio of Ca to Al is at least 0.35:10 and the molar ratio of glycine to Al is no more than 1.7:10. The molar ratio of Ca to Al is more preferably at least 0.40:10 and most preferably at least 0.45:1, each in combination with the molar ratio of glycine to Al being no more than 1.7:10 and more preferably no more than 1.5:10.

Herein, references to molar amounts and ratios of "aluminium" are calculated on the basis of mono-nuclear aluminium, but include aluminium present in poly-nuclear species; indeed, most of the aluminium in the salts of relevance is present in poly-nuclear species.

The above indicated preferences for calcium to aluminium molar ratio and/or glycine to aluminium molar ratio lead to compositions of acceptable Band III content (vide infra) and surprisingly good antiperspirancy performance for the levels of calcium and glycine employed.

It is noteworthy that glycine must be used in order to activate the antiperspirant salt. The combination of a water-soluble calcium salt and a hydroxy acid, as disclosed in EP 1,104,282 (Gillette) or alternative amino acids is not a feature of the present invention.

The activation process generally produces a mixture of aluminium species having a relatively high content of what is commonly termed Band III material, as determined by SEC (Size Exclusion Chromatography) analysis. The SEC technique employed is well known in the art and is described in further detail in U.S. Pat. No. 4,359,456 (Gosling). The SEC band commonly referred to as Band III is designated as "Peak 4" in EP 1,104,282 B1 by Gillette.

Herein, "Band III content" refers to the integrated area in the Band III region of the SEC chromatograph relative to the total integrated area in all of the regions corresponding to aluminium species; that is to say, Bands I, II, III, and IV.

Compositions according to the invention preferably comprise aluminium species having a Band III content of at least 27%. Surprisingly, we have found that good antiperspirancy can be achieved with actives having a Band III content not significantly greater than this, indeed particularly preferred compositions have a Band III content of from 27% to 45%, or even 27% to 39%.

In the activation process and method of manufacture described herein, it is preferred that the activation mixture is heated for sufficient time for the Band III content of the aluminium species to become at least 27% and preferably no more than 45%.

In the activation process and method of manufacture described herein, the activation mixture is heated to at least 65° C., preferably to at least 75° C., and more preferably to at least 85° C.

The processes described herein produce an aqueous solution of an activated antiperspirant salt. It will be realised, however, that such solutions may be dried by techniques known in the art, notably spray drying, to give a dried antiperspirant salt. Such dried antiperspirant salts may be used in a variety of compositions, including aerosols, sticks and soft solids. Such compositions are also to be considered antiperspirant compositions according to the invention. It will be realised that such compositions may be essentially anhydrous, having less than 1% by weight of free water or may be anhydrous, having less than 0.1% by weight of free water.

The benefits of the present invention are especially relevant to concentrated aqueous solutions, in particular aqueous solutions having a total anhydrous solids content of 20% or greater and especially aqueous solutions having a total anhydrous solids content of 30% or greater.

The benefits of the present invention are particularly relevant to the manufacture of antiperspirant actives and/or compositions involving the use of aqueous solutions having a total anhydrous solids content of 20% or greater and especially to the manufacture of antiperspirant actives and/or compositions involving the use of aqueous having a total anhydrous solids content of 30% or greater. The anhydrous solids referred to herein are typically the BAC salt, calcium chloride and glycine.

The total anhydrous solids referred to herein are typically BAC salt, calcium chloride and glycine.

Herein, "free water" excludes any water of hydration associated with the antiperspirant salt or other component added to a particular composition, but includes all other water present.

Herein, compositions according to the invention intended for use as antiperspirant compositions are termed "antiperspirant compositions".

Other components may also be including in antiperspirant compositions according to the invention.

Herein, amounts and concentrations of ingredients are percentages by weight of the total composition, unless otherwise indicated and ratios are ratios by weight.

A preferred additional component of compositions of the invention is an oil.

Herein, the terms "oil" and signifies a water-insoluble organic material that is liquid at 20° C. Any material having a solubility of less than 0.1 g/100 g at 20° C. is considered to be insoluble.

Herein "aqueous compositions" are compositions having a continuous phase that is predominately water; that is to say, greater than 50% water.

A preferred oil for use in accordance with the present invention is a fragrance oil, sometimes alternatively called a perfume oil. The fragrance oil may comprise a single fragrance or component more commonly a plurality of fragrance components. Herein, fragrance oils impart an odour, preferably a pleasant odour, to the composition. Preferably, the fragrance oil imparts a pleasant odour to the surface of the human body the composition is applied to the same.

The amount of fragrance oil in the composition is commonly up to 3% advantageously is at least 0.5% and particularly from 0.8% to 2%.

The total amount of oil in the composition is preferably from 0.1 to 20%, more preferably from 0.5 to 10%, and most preferably at from 2 to 8% by weight of the total composition. In certain preferred embodiments, particularly those also comprising an aluminium and/or zirconium containing antiperspirant active, the oil is present at greater than 2.5% and less than 6% by weight of the total composition.

In certain embodiments, it is preferred to include an oil, other than a fragrance oil, that has a relatively low viscosity, by which is meant less 250 cS (mm$^2 \cdot $s$^{-1}$). Such oils can improve the sensory properties of the composition on application and can lead to other benefits such as emolliency.

Suitable oils can be selected from alkyl ether oils having a boiling point of above 100° C. and especially above 150° C., including polyalkyleneglycol alkyl ethers. Such ethers desirably comprise between 10 and 20 ethylene glycol or propylene glycol units and the alkyl group commonly contains from 4 to 20 carbon atoms. The preferred ether oils include polypropylene glycol alkyl ethers such as PPG-14-butylether and PPG-15-stearyl ether.

Suitable oils can include one or more triglyceride oils. The triglyceride oils commonly comprise the alkyl residues of aliphatic $C_7$ to $C_{20}$ alcohols, the total number of carbon atoms being selected in conjunction with the extent of olefinic unsaturation and/or branching to enable the triglyceride to be liquid at 20° C. One example is jojoba oil. Particularly preferably, in the triglyceride oil the alkyl residues are linear $C_{18}$ groups having one, two or three olefinic degrees of unsaturation, two or three being optionally conjugated, many of which are extractable from plants (or their synthetic analogues), including triglycerides of oleic acid, linoleic acid, conjugated linoleic acids, linolenic acid, petroselenic acid, ricinoleic acid, linolenelaidic acid, trans 7-octadecenoic acid, parinaric acid, pinolenic acid, punicic acid, petroselenic acid and stearidonic acid.

Suitable oils can include those derived from unsaturated $C_{18}$ acids, including coriander seed oil, impatiens balsimina seed oil, parinarium laurinarium kernel fat oil, sabastiana brasilinensis seed oil, dehydrated castor seed oil, borage seed oil, evening primrose oil, aquilegia vulgaris oil, sunflower (seed) oil and safflower oil. Other suitable oils are obtainable from hemp, and maize corn oil. An especially preferred oil by virtue of its characteristics is sunflower (seed) oil.

Further suitable oils, that can also be emollient oils, comprise alkyl or alkyl-aryl ester oils having a boiling point of above 150° C. (and a melting point of below 20° C.). Such ester oils include oils containing one or two alkyl groups of 12 to 24 carbon atoms length, including isopropyl myristate, isopropyl palmitate and myristyl palmitate. Other non-volatile ester oils include alkyl or aryl benzoates such $C_{12-15}$ alkyl benzoate, for example Finsolv TN™ or Finsolv Sun™.

A further class of suitable oils comprises non-volatile dimethicones, often comprising phenyl or diphenylene substitution, for example Dow Corning 200 350 cps or Dow Corning 556.

A preferred component in many antiperspirant compositions, particularly aqueous antiperspirant compositions, according to the invention is an emulsifier. Emulsifiers are particularly advantageous in aqueous systems additionally comprising fragrance oil and/or other oil.

Preferred compositions according to the invention are oil-in-water emulsions comprising an emulsifier, such compositions giving especially effective antiperspirancy, especially when the molar ratio of calcium to aluminium and/or glycine to aluminium is within the preferred ranges indicated above (vide supra).

It is preferred that emulsifiers used in aqueous antiperspirant compositions of the present invention form a lamellar phase emulsifier system in the composition.

Such systems may be readily identified by means of optical microscopy. Such systems lead to good emulsion stability in compositions according to the invention.

It is preferred that aqueous antiperspirant compositions of the present invention comprise a non-ionic emulsifier system. Such an emulsifier system conveniently has a mean HLB value in the region of from about 5 to about 12 and particularly from 6 to about 10. In the preferred embodiments referred to in the paragraph immediately above, an especially desired mean HLB value is from 6 to 9. Such a mean HLB value can be provided by selecting an emulsifier having such an HLB value, or more preferably by employing a combination of at least two emulsifiers, a first (lower) HLB emulsifier having an HLB value in the range of from 2 to 6.5, such as in particular from 4 to 6 and a second (higher) HLB emulsifier having an HLB value in the range of from about 6.5 to 18 and especially from about 12 to about 18. When a combination of emulsifiers is employed, the average HLB value can be calculated as a weight average of the HLB values of the constituent emulsifiers.

Lamellar phase emulsifier systems preferably comprise two non-ionic surfactants, optionally selected as suggested in the paragraph immediately above. In a particular embodiment a first emulsifier is a fatty alcohol, such as cetyl and/or stearyl alcohol and a second emulsifier is much more hydrophilic, having a HLB of from about 6.5 to 18 and especially from about 12 to about 18.

An especially desirable range of emulsifiers comprises a hydrophilic moiety provided by a polyalkylene oxide (polyglycol), and a hydrophobic moiety provided by an aliphatic hydrocarbon, preferably containing at least 10 carbons and commonly linear. The hydrophobic and hydrophilic moieties can be linked via an ester or ether linkage, possibly via an intermediate polyol such as glycerol. A preferred range of emulsifiers comprises polyethylene glycol ethers.

Preferably the hydrophobic aliphatic substituent contains at least 12 carbons, and is derivable from lauryl, palmityl, cetyl, stearyl, and behenyl alcohol, and especially cetyl, stearyl or a mixture of cetyl and stearyl alcohols or from the corresponding carboxylic acids.

The polyalkylene oxide is often selected from polyethylene oxide and polypropylene oxide or a copolymer of ethylene oxide and especially comprises a polyethylene oxide. The number of alkylene oxide and especially of ethoxylate units within suitable emulsifiers is often selected within the range of from 2 to 100. Emulsifiers with a mean number of ethoxylate units in the region of 2 can provide a lower HLB value of below 6.5 and those having at least 4 such units provide a higher HLB value of above 6.5 and especially those containing at least 10 ethoxylate units which provide an HLB value of above 10. A preferred combination comprises a mixture of an ethoxylate containing 2 units and one containing from 10 to 40 units, such as from 15 to 30 or desirably from 20 to 25. Particularly conveniently, the combination of emulsifiers comprises steareth-2 and a selection from steareth-15 to steareth-30.

It is desirable to employ a mixture of ethoxylated alcohol emulsifiers in a weight ratio of emulsifier having a lower HLB value of less than 6.5 to emulsifier having a higher HLB value of greater than 8 of from 2:1 to 6:1 and particularly from 4:1 to 6:1.

The total proportion of emulsifiers in the composition is usually at least 1% and particularly at least 2% by weight. Commonly, the emulsifiers are not present at above 10%, often not more than 7% by weight and in many preferred embodiments up to 6% by weight. An especially desirable concentration range for the emulsifiers is from 2.5 to 5% by weight.

Other components that may be present include short chain ($C_2$-$C_4$) alcohols and especially polyols such glycerol, ethylene glycol, propylene glycol and polymers thereof, in particular poly(ethylene glycol) and poly(propylene glycol). Poly(ethylene glycol) of average molecular weight 200 to 600 is a preferred component. Such components may add to the sensory properties of the composition and, when included, are typically present at from 0.5 to 10% of the total composition.

The aqueous compositions of the present invention are very suitable for dispensing via a roll-on dispenser, for example any upright dispenser such as described in EP1175165 or an invert dispenser such as described in U.S. Pat. No. 6,511,243 or WO05/007377. Invert indicates that the dispenser stands stably with its dispensing ball below the formulation reservoir. In using such dispensers, the composition is applied by rolling the ball of the dispenser across the skin surface, depositing a film of fluid on the skin. Commonly the dispenser is wiped across the skin between 4 and 10 strokes. Commonly from 0.2 to 0.5 g of the composition is deposited in each armpit per application.

The method of attaining an antiperspirant benefit described as the third aspect of the invention (vide supra) may involve direct or indirect topical application to the composition surface of the human body. In a related method, a composition comprising an antiperspirant salt prepared by drying an antiperspirant solution prepared according to the second aspect of the invention may be topically applied to the surface of the human body, directly or indirectly. In each of the methods described in this paragraph, the composition is preferably applied to the underarm regions of the human body.

EXAMPLES

In the following examples, all percentages are by weight, unless otherwise indicated.

Comparative examples are indicated by codes starting with a letter and examples according to the invention by codes starting with a number.

Materials

The ASCH used was Reach 301 L from Summit. This contained 40% anhydrous active. The ASCH had an approximate general formula of $Al_2(OH)_{4.8}Cl_{1.2}$ and an Al:Cl ratio of approximately 1.67:1. The calcium chloride dihydrate and glycine were ex Sigma-Aldrich. Additional water was deionised.

Methods of Preparation

The examples indicated in Table 1 were prepared by dispensing the required amounts of ASCH, water and calcium chloride dihydrate into glass bottles and allowing to dissolve. The glycine was then added and dissolved. No heating was used and dissolution was aided by gentle swirling/shaking.

The solutions were heated for one hour at 86+/−1° C. Heat up time to 86° C. was less than one hour and cooling back to room temperature was also achieved within one hour.

HPLC Band analysis was carried out after one day on samples stored at 20° C. Not all examples were tested, but the results for those that were are given in Table 2.

TABLE 1

Compositions of solutions made with 28.11% ASCH (anhydrous)

Solution concentration wt. %, all as anhydrous solids

| Example | Al | Ca | Glycine | ASCH | CaCl$_2$ | Glycine | Total Solids |
|---|---|---|---|---|---|---|---|
| A1a | 10 | 1.34 | 6.20 | 28.11 | 4.68 | 14.68 | 47.47 |
| A2a | 10 | 1.00 | 4.65 | 28.11 | 3.51 | 11.01 | 42.63 |
| A3a | 10 | 0.75 | 3.49 | 28.11 | 2.64 | 8.26 | 39.00 |
| A4a | 10 | 0.50 | 2.33 | 28.11 | 1.76 | 5.50 | 35.37 |
| A5a | 10 | 1.67 | 4.65 | 28.11 | 5.86 | 11.01 | 44.98 |
| A6a | 10 | 1.50 | 4.65 | 28.11 | 5.27 | 11.01 | 44.39 |
| A7a | 10 | 0.75 | 4.65 | 28.11 | 2.64 | 11.01 | 41.75 |
| A8a | 10 | 0.50 | 4.65 | 28.11 | 1.76 | 11.01 | 40.88 |
| A9a | 10 | 1.00 | 7.75 | 28.11 | 3.51 | 18.35 | 49.97 |
| A10a | 10 | 1.00 | 6.98 | 28.11 | 3.51 | 16.51 | 48.14 |
| A11a | 10 | 1.00 | 2.33 | 28.11 | 3.51 | 5.50 | 37.13 |
| A12a | 10 | 1.34 | 2.33 | 28.11 | 4.68 | 5.50 | 38.30 |
| A13a | 10 | 1.67 | 2.33 | 28.11 | 5.86 | 5.50 | 39.47 |
| A14a | 10 | 0.50 | 1.74 | 28.11 | 1.76 | 4.13 | 34.00 |
| A15a | 10 | 0.75 | 1.74 | 28.11 | 2.64 | 4.13 | 34.87 |
| A16a | 10 | 0.60 | 1.98 | 28.11 | 2.11 | 4.68 | 34.90 |
| B1a | 10 | 2.01 | 1.17 | 28.11 | 7.03 | 2.76 | 37.90 |
| B2a | 10 | 1.67 | 1.17 | 28.11 | 5.86 | 2.76 | 36.73 |
| B3a | 10 | 2.01 | 2.33 | 28.11 | 7.03 | 5.50 | 40.64 |
| C1a | 10 | 0.25 | 1.17 | 28.11 | 0.88 | 2.75 | 31.74 |
| C2a | 10 | 1.00 | 0.58 | 28.11 | 3.51 | 1.38 | 33.00 |
| 1a | 10 | 1.00 | 1.16 | 28.11 | 3.51 | 2.75 | 34.38 |
| 2a | 10 | 1.34 | 1.17 | 28.11 | 4.68 | 2.75 | 35.55 |
| 3a | 10 | 0.25 | 1.74 | 28.11 | 0.88 | 4.13 | 33.12 |
| 4a | 10 | 0.50 | 1.17 | 28.11 | 1.76 | 2.75 | 32.62 |
| 5a | 10 | 0.75 | 1.17 | 28.11 | 2.64 | 2.75 | 33.50 |
| 6a | 10 | 0.67 | 1.44 | 28.11 | 2.34 | 3.40 | 33.85 |

TABLE 2

Storage stability and Band analysis of solutions detailed in Table 1

| | Solution Stability | | | HPLC Band Analysis (after 1 day at 20° C.) | |
|---|---|---|---|---|---|
| | At 20° C. | | At 45° C. | | |
| Example | Days | Failure Mode | Days | Failure Mode | % Band III | Band III %/Band 2 |
| A1a | 4 | Hazy gel | 4 | Hazy gel | — | — |
| A2a | 7 | Hazy gel | 4 | Hazy gel | 57 | 3.50 |
| A3a | 7 | Hazy gel | 4 | Hazy gel | — | — |
| A4a | 14 | Hazy gel | 14 | Hazy gel | — | — |
| A5a | 7 | Hazy gel | 4 | Hazy gel | — | — |
| A6a | 7 | Hazy gel | 4 | Hazy gel | — | — |
| A7a | 4 | Hazy gel | 1 | Hazy gel | — | — |

TABLE 2-continued

Storage stability and Band analysis of solutions detailed in Table 1

| | Solution Stability | | | | HPLC Band Analysis | |
| | At 20° C. | | At 45° C. | | (after 1 day at 20° C.) | |
| Example | Days | Failure Mode | Days | Failure Mode | % Band III | Band III %/ Band 2 |
|---|---|---|---|---|---|---|
| A8a | 0 | Hazy gel | 0 | Hazy gel | — | — |
| A9a | 7 | Hazy gel | 4 | Hazy gel | — | — |
| A10a | 7 | Hazy gel | 4 | Hazy gel | — | — |
| A11a | 14 | Hazy gel | 14 | Hazy gel | — | — |
| A12a | 14 | Hazy gel | 28 | Hazy gel | — | — |
| A13a | 28 | Hazy gel | 28 | Hazy gel | — | — |
| A14a | 56 | Hazy gel | >196 | None | 36 | 0.90 |
| A15a | 56 | Hazy gel | >196 | None | 39 | 1.16 |
| A16a | 28 | Hazy gel | >56 | None | 39 | 1.03 |
| B1a | 14 | Gel | 56 | Gel | 62 | 4.95 |
| B2a | 56 | Precipitate | >252 | None | 30 | 0.82 |
| B3a | 1 | Gel | 1 | Gel | — | — |
| C1a | >196 | None | >196 | None | 25 | 0.45 |
| C2a | >196 | None | >196 | None | 20 | 0.41 |
| 1a | >252 | None | >252 | None | 31 | 0.77 |
| 2a | >252 | None | >252 | None | 31 | 0.83 |
| 3a | 168 | Hazy gel | >196 | None | 28 | 0.58 |
| 4a | >196 | None | >196 | None | 27 | 0.57 |
| 5a | >196 | None | >196 | None | 30 | 0.71 |
| 6a | >122 | None | >122 | None | 37 | 0.97 |

The solutions as detailed in Table 1 were stored in 20° C. and 45° C. in thermostatically controlled storage cabinets. Storage stability was assessed by visual inspection and the results are presented in Table 2. Assessments were made at 1 day, 4 days, 14 days, 28 days, and then at further 28 day intervals. A reported failure time of 56 days thus indicates that the solution failed at some point between 28 days and 56 days. The "failure mode" indicates the visual appearance of the sample. The failure mode indicated by "gel" was preceded by a white precipitate. Please note that only were a "failure mode" is indicated was a failure observed and that total test periods differed from sample to sample at the time of reporting.

The results given in Table 2 illustrate that comparative examples A1a to A16a all failed due to lack of stability to gelation at 20° C. and generally at 45° C. as well. Comparative Examples B1a to B3a all failed due to the formation of a white precipitate in the solution, in some cases converting to a white gel. Comparative Examples C1a and C2a showed acceptable stability, but had inferior Band 3 levels.

Examples 1a to 5a all demonstrated enhanced storage stability relative to the controls and had acceptable Band 3 levels. Whilst Examples 3a did eventually fail at 20° C. due to the formation of a hazy gel, this was after 168 days, far longer than for any of Comparative Examples A1a to A16a or Comparative Examples B1a to B3a.

Examples 1a and 6a were formulated into roll-on compositions and shown to give excellent antiperspirancy benefits. When formulated at an active level of 12% by weight of anhydrous ASCH, Example 1a gave an SWR (sweat weight reduction) of 58% and Example 6a gave an SWR of 60%. These figures are surprisingly high for systems having relatively low Band III contents.

The examples indicated in Table 3 were prepared in an analogous manner to those detailed in Table 1.

HPLC Band analysis for the examples detailed in Table 3 are given in Table 4, together with their storage stability results, assessed as for the examples detailed in Table 1. In broad terms, the results indicated in Table 4 reflect those in Table 2, indicating that the stability benefits attained with the present invention span a wide range of concentrations.

TABLE 3

Compositions of solutions made with 18.83% ASCH (anhydrous)

| | Mole Ratio | | | Solution concentration wt. %, all as anhydrous solids | | | |
|---|---|---|---|---|---|---|---|
| Example | Al | Ca | Glycine | ASCH | CaCl$_2$ | Glycine | Total Solids |
| A2b | 10 | 1.00 | 4.65 | 18.83 | 2.35 | 7.38 | 28.56 |
| A4b | 10 | 0.50 | 2.33 | 18.83 | 1.18 | 3.69 | 23.70 |
| A11b | 10 | 1.00 | 2.33 | 18.83 | 2.35 | 3.69 | 24.87 |
| A12b | 10 | 1.34 | 2.33 | 18.83 | 3.14 | 3.69 | 25.66 |
| A13b | 10 | 1.67 | 2.33 | 18.83 | 3.92 | 3.69 | 26.44 |
| A14b | 10 | 0.50 | 1.74 | 18.83 | 1.18 | 2.77 | 22.77 |
| A15b | 10 | 0.75 | 1.74 | 18.83 | 1.77 | 2.77 | 23.36 |
| A16b | 10 | 0.60 | 1.98 | 18.83 | 1.41 | 3.14 | 23.38 |
| B1b | 10 | 2.01 | 1.17 | 18.83 | 4.71 | 1.85 | 25.39 |
| B2b | 10 | 1.67 | 1.17 | 18.83 | 3.92 | 1.85 | 24.61 |
| B3b | 10 | 2.01 | 2.33 | 18.83 | 4.71 | 3.69 | 27.23 |
| C1b | 10 | 0.25 | 1.17 | 18.83 | 0.59 | 1.84 | 21.26 |
| C2b | 10 | 1.00 | 0.58 | 18.83 | 2.35 | 0.92 | 22.11 |
| 1b | 10 | 1.00 | 1.16 | 18.83 | 2.35 | 1.84 | 23.03 |
| 2b | 10 | 1.34 | 1.17 | 18.83 | 3.14 | 1.84 | 23.81 |
| 3b | 10 | 0.25 | 1.74 | 18.83 | 0.59 | 2.77 | 22.18 |
| 4b | 10 | 0.50 | 1.17 | 18.83 | 1.18 | 1.84 | 21.85 |
| 5b | 10 | 0.75 | 1.17 | 18.83 | 1.77 | 1.84 | 22.44 |
| 6b | 10 | 0.67 | 1.44 | 18.83 | 1.57 | 2.28 | 22.68 |

TABLE 4

Storage stability and Band analysis of solutions detailed in Table 3

| | Solution Stability | | | | HPLC Band Analysis | |
| | At 20° C. | | At 45° C. | | (after 1 day at 20° C.) | |
| Example | Days | Failure Mode | Days | Failure Mode | % Band 3 | % Band 3/ % Band 2 |
|---|---|---|---|---|---|---|
| A2b | 56 | Hazy gel | >168 | None | 62 | 4.95 |
| A4b | 56 | Hazy gel | >168 | None | 39 | 1.00 |
| A11b | 28 | Hazy gel | >168 | None | 47 | 1.86 |
| A12b | 28 | Hazy gel | >168 | None | 48 | 2.30 |
| A13b | 28 | Hazy gel | >168 | None | 50 | 2.85 |
| A14b | 168 | Hazy gel | >168 | None | 35 | 0.87 |
| A15b | 84 | Hazy gel | >168 | None | 39 | 1.16 |
| A16b | 56 | Hazy gel | >56 d | None | 42 | 1.13 |
| B1b | >168 | None | >168 | None | 31 | 0.97 |
| B2b | >168 | None | >168 | None | 31 | 0.95 |
| B3b | 84 | Hazy gel | >168 | None | 50 | 3.85 |
| C1b | >168 | None | >168 | None | 24 | 0.44 |
| C2b | >168 | None | >168 | None | 21 | 0.43 |
| 1b | >168 | None | >168 | None | 31 | 0.76 |
| 2b | >168 | None | >168 | None | 31 | 0.85 |
| 3b | >168 | None | >168 | None | 27 | 0.54 |
| 4b | >168 | None | >168 | None | 29 | 0.62 |
| 5b | >168 | None | >168 | None | 31 | 0.75 |
| 6b | >84 | None | >84 | None | 41 | 1.16 |

The invention claimed is:

1. An aqueous composition comprising:
(i) basic aluminium chloride (BAC) salt of formula $Al_2(OH)_{4.4}Cl_{1.6}$ to $Al_2(OH)_{4.9}Cl_{1.1}$,
(ii) calcium chloride at a molar level of 0.020 or greater relative to the aluminium present in the BAC salt, and
(iii) glycine at a molar level of 0.050 or greater relative to the aluminium present in the BAC salt,
characterised in that the molar ratio of aluminium to the sum of the molar amounts of the calcium chloride and glycine is from 3.9:1 to 6.1:1 and in that:

(a) the molar ratio of glycine to Al is at least 1.7:10 and the molar ratio of Ca to Al is no more than 0.35:10 or (b) the molar ratio of Ca to Al is at least 0.35:10 and the molar ratio of glycine to Al is no more than 1.7:10.

2. The composition according to claim 1, wherein the BAC salt is of formula $Al_2(OH)_{4.7}Cl_{1.3}$ to $Al_2(OH)_{4.9}Cl_{1.1}$.

3. The composition according to claim 1, wherein calcium chloride is present at a molar level of 0.025 or greater relative to the aluminium present in the BAC salt.

4. The composition according to claim 1, wherein glycine is present at a molar level of 0.1 or greater relative to the aluminium present in the BAC salt.

5. The composition according to claim 1, wherein molar ratio of aluminium to the sum of the molar amounts of the calcium chloride and glycine is from 4.0:1 to 6.0:1.

6. The composition according to claim 1, wherein the molar ratio of glycine to Al is at least 1.7:10 and the molar ratio of Ca to Al is no more than 0.35:10.

7. The composition according to claim 1, wherein the molar ratio of Ca to Al is at least 0.35:10 and the molar ratio of glycine to Al is no more than 1.7:10.

8. The composition according to claim 7, wherein the molar ratio of Ca to Al is at least 0.40:10.

9. The composition according to claim 7, wherein the molar ratio of glycine to Al is no more than 1.5:10.

10. The composition according to claim 7, wherein the molar ratio of Ca to Al is at least 0.45:10.

11. The composition according to claim 1, further comprising a total anhydrous solids content of the composition of 20% or greater.

12. The composition according to claim 11 wherein the total anhydrous solids content of the composition is 30% or greater.

13. The composition according to claim 1, wherein the BAC salt has a Band III content measured by Size Exclusion Chromatography (SEC) of from 27% to 45%.

14. A roll-on dispenser comprising the composition according to claim 1.

15. An anhydrous composition comprising a spray dried antiperspirant salt of the composition according to claim 1.

16. A method of manufacture of an aqueous antiperspirant composition, the method comprising:

(i) mixing basic aluminium chloride (BAC) salt of formula $Al_2(OH)_{4.4}Cl_{1.6}$ to $Al_2(OH)_{4.9}Cl_{1.1}$, calcium chloride at a molar level of 0.020 or greater relative to the aluminium present in the BAC salt, glycine at a molar level of 0.050 or greater relative to the aluminium present in the BAC salt, and water, such that the molar ratio of aluminium to the sum of the molar amounts of the calcium chloride and glycine is from 3.9:1 to 6.1:1; and (a) the molar ratio of glycine to Al is at least 1.7:10 and the molar ratio of Ca to Al is no more than 0.35:10 or (b) the molar ratio of Ca to Al is at least 0.35:10 and the molar ratio of glycine to Al is no more than 1.7:10; wherein the molar ratio of AL to the sum of the molar amounts of the calcium chloride and glycine is from 3.9:1 to 6.1:1;

(ii) heating the mixture to a temperature of at least 65° C. for at least 2 hours, and (iii) cooling the mixture to ambient temperature.

17. The method of manufacture according to claim 16, wherein the mixture has a total anhydrous solids content of 20% or greater.

18. The method according to claim 16 wherein the mixture has a total anhydrous solids content of 30% or greater.

* * * * *